United States Patent
Tsai et al.

(10) Patent No.: US 7,914,753 B2
(45) Date of Patent: Mar. 29, 2011

(54) ANALYTICAL SYSTEM, AND ANALYTICAL METHOD AND FLOW STRUCTURE THEREOF

(75) Inventors: Chung-Hsien Tsai, Taipei County (TW); Chin-Tai Tseng, Changhua County (TW); Chien-Chih Huang, Taipei County (TW); Wen-Pin Hsieh, Miaoli County (TW); Hsiao-Chung Tsai, Changhua County (TW); Cheng-Yu Ko, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/326,860

(22) Filed: Dec. 2, 2008

(65) Prior Publication Data

US 2009/0298092 A1    Dec. 3, 2009

(30) Foreign Application Priority Data

May 28, 2008  (TW) ................................ 97119687 A

(51) Int. Cl.
  *G01N 33/53* (2006.01)
(52) U.S. Cl. .......... 422/506; 422/72; 422/501; 436/177; 436/180; 494/85; 435/287.1; 435/288.3
(58) Field of Classification Search .................... 422/72, 422/100; 436/180, 177; 494/85; 435/287.1, 435/288.3
See application file for complete search history.

(56) References Cited

U.S. PATENT DOCUMENTS

| | | | |
|---|---|---|---|
| 3,901,658 A | 8/1975 | Burtis et al. | |
| 5,061,381 A | 10/1991 | Burd | |
| 5,089,417 A | 2/1992 | Wogoman | |
| 5,122,284 A | 6/1992 | Braynin et al. | |
| 5,186,844 A | 2/1993 | Burd et al. | |
| 5,304,348 A | 4/1994 | Burd et al. | |
| 5,693,233 A | 12/1997 | Schembri | |
| 5,916,522 A | 6/1999 | Boyd et al. | |
| 6,548,788 B2 | 4/2003 | Kellogg et al. | |
| 7,026,131 B2 | 4/2006 | Hurt et al. | |
| 7,033,747 B2 | 4/2006 | Gordon | |
| 2006/0133958 A1 | 6/2006 | Hsieh et al. | |

OTHER PUBLICATIONS

Carl A. Burtis et al. "Development of a Simple Device for Processing Whole-Blood Samples into Measured Aliquots of Plasma", Clinical Chemistry, vol. 32, No. 9, 1986, pp. 1642-1647, US.
Chinese Patent Office, Office Action, Chinese Patent Application Serial No. 200810109929.2, Nov. 25, 2010, China.

*Primary Examiner* — Jill Warden
*Assistant Examiner* — Shogo Sasaki

(57) ABSTRACT

An analytical system includes a working fluid, a uniform dividing unit and a separating unit. The working fluid includes a first component and a second component with different characteristics. The uniform dividing unit is utilized to uniformly divide the working fluid and relatively rotated with respect to a reference axis. Under a capillarity force as well as the result of Coriolis force and siphon force, the first component can be separated from the second component by the separating unit.

33 Claims, 14 Drawing Sheets

ANALYTICAL SYSTEM, AND ANALYTICAL METHOD AND FLOW STRUCTURE THEREOF

CROSS REFERENCE TO RELATED APPLICATIONS

This Application claims priority of Taiwan Patent Application No. 097119687, filed on May 28, 2008, the entirety of which is incorporated by reference herein.

BACKGROUND OF THE INVENTION

1. Field of the Invention

The present invention relates to a flow structure, and in particular relates to an analytical system, and analytical method and flow structure capable of utilizing an inertial force (e.g., Coriolis force) generated by an inertia phenomena (e.g., Coriolis acceleration) by a rotating element to result in a fluid reaction, wherein separation of a tested specimen comprising different components with different characteristics are performed.

2. Description of the Related Art

In general, a conventional fluid separation device has a complicated structure. U.S. Pat. No. 6,548,788, for example, discloses methods and an apparatus for performing microanalytic and microsynthetic analyses and procedures. The fluid separation apparatus comprises a microchannel to control the movement of fluid. However, the microchannel must be manufactured by using micromaching technology. Thus, when compared with plastic injection technology, the cost of the fluid separation apparatus is high.

U.S. Pat. Nos. 5,061,381 and 5,089,417 also disclose fluid separation devices having complicated structures and high manufacturing costs.

BRIEF SUMMARY OF THE INVENTION

The invention provides a flow structure with a simple structure capable of decreasing manufacturing costs for fluid separation devices. The flow structure of the invention is suitable for performing separation of a tested specimen comprising a first component and a second component with different characteristics therebetween. The flow structure comprises a first compartment, a second compartment, a third compartment and a fourth compartment.

The second compartment is communicated with the first compartment and rotated with respect to a reference axis. The tested specimen is transmitted to the second compartment when the tested specimen is disposed in the first compartment. The third compartment communicated with the second compartment comprises a first cushion region and a second cushion region connects to the first cushion region. The tested specimen located at the second compartment is transmitted to the third compartment at a first predetermined period of time when the second compartment is rotated with respect to the reference axis in a first direction, and the separation of the first and second components of the tested specimen located at the first cushion region of the third compartment is performed at a second predetermined period of time. The first predetermined period of time is prior to the second predetermined period of time, and the second cushion region of the third compartment is filled with the separated first component. The fourth compartment is communicated with the third compartment. The first component of the tested specimen located at the second cushion region of the third compartment is transmitted to the fourth compartment when the rotating second compartment is stopped with respect to the reference axis and delayed after a particular period of time. The separated first component located at the fourth compartment is outwardly transmitted by an acting force via the fourth compartment when the second compartment that was stopped and begins to rotate in a second direction different from the first direction with respect to the reference axis, so that the first component is completely separated from the second component.

Further, the invention provides an analytical system. The analytical system comprises a working fluid, a uniform dividing unit, a separation unit and a centrifugal chamber.

The working fluid comprises a first component and a second component with different characteristics. The uniform dividing unit relatively rotated with respect to a reference axis is utilized to uniformly divide the working fluid. The separation unit utilized to centrifugally separate the first and second components of the working fluid located at the uniform dividing unit comprises a centrifugal chamber and a separation channel. The centrifugal chamber comprising a first cushion region and a second cushion region connects to the first cushion region. The working fluid located at the uniform dividing unit is transmitted to the centrifugal chamber at a first predetermined period of time when the uniform dividing unit is rotated with respect to the reference axis in a first direction, and the separation of the first and second components of the working fluid located at the first cushion region of the centrifugal chamber is performed at a second predetermined period of time. The first predetermined period of time is prior to the second predetermined period of time, and the second cushion region of the centrifugal chamber is filled with the separated first component. The separation channel is communicated with the centrifugal chamber. The first component of the working fluid located at the first cushion region and the second cushion region of the centrifugal chamber is transmitted to the separation channel when the rotating uniform dividing unit is stopped with respect to the reference axis and delayed after a particular period of time, and the separated first component located at the separation channel is outwardly transmitted by an acting force via the separation channel when the uniform dividing unit that was stopped begins to rotate in a second direction different from the first direction with respect to the reference axis, so that the first component is completely separated from the second component.

Additionally, the invention provides an analytical method. The analytical method comprises the steps of: providing a working fluid comprising a first component and a second component with different characteristics providing a uniform dividing unit relatively rotated with respect to a reference axis to uniformly divide the working fluid and providing a centrifugal chamber and a separation channel to centrifugally separate the first and second components of the working fluid located at the uniform dividing unit. The centrifugal chamber comprises a first cushion region and a second cushion region connecting to the first cushion region.

The working fluid located at the uniform dividing unit is transmitted to the centrifugal chamber at a first predetermined period of time when the uniform dividing unit is rotated with respect to the reference axis in a first direction, and the separation of the first and second components of the working fluid located at the first cushion region of the centrifugal chamber is performed at a second predetermined period of time. The first predetermined period of time is prior to the second predetermined period of time, and the second cushion region of the centrifugal chamber is filled with the separated first component. The separation channel is communicated with the centrifugal chamber. The first component of the working fluid located at the first cushion region and the second cushion region of the centrifugal chamber is transmitted to the separation channel when the rotating uniform dividing unit is stopped with respect to the reference axis and delayed after a particular period of time, and the separated first component located at the separation channel is outwardly transmitted by an acting force via the separation channel when the uniform dividing unit that was stopped begins to rotate in a second direction different from the first direction with respect to the reference axis, so that the first component is completely separated from the second component.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
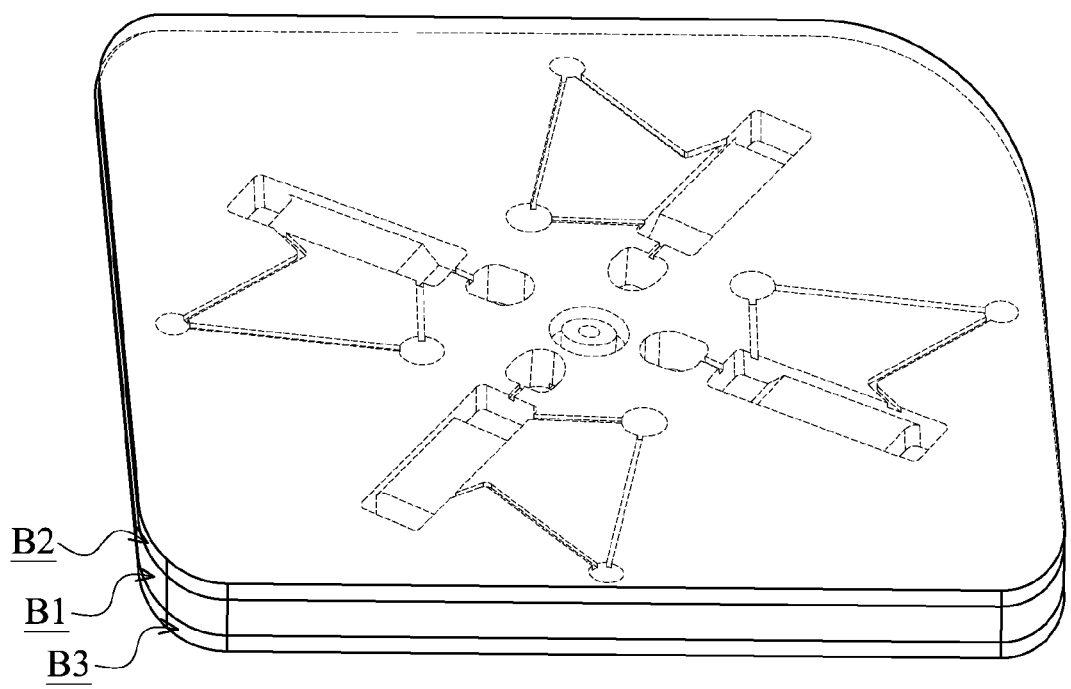
FIG. 1A is an assembled perspective view of a flow structure of the invention.

The following description is made for the purpose of illustrating the general principles of the invention and should not be taken in a limiting sense. The scope of the invention is best determined by reference to the appended claims.

The invention provides a flow structure with a simple structure capable of decreasing manufacturing costs for fluid separation devices. The flow structure of the invention is suitable for performing separation of a tested specimen comprising a first component and a second component with different characteristics therebetween. The flow structure comprises a first compartment, a second compartment, a third compartment and a fourth compartment.

The second compartment is communicated with the first compartment and rotated with respect to a reference axis. The tested specimen is transmitted to the second compartment when the tested specimen is disposed in the first compartment. The third compartment communicated with the second compartment comprises a first cushion region and a second cushion region connects to the first cushion region. The tested specimen located at the second compartment is transmitted to the third compartment at a first predetermined period of time when the second compartment is rotated with respect to the reference axis in a first direction, and the separation of the first and second components of the tested specimen located at the first cushion region of the third compartment is performed at a second predetermined period of time. The first predetermined period of time is prior to the second predetermined period of time, and the second cushion region of the third compartment is filled with the separated first component. The fourth compartment is communicated with the third compartment. The first component of the tested specimen located at the second cushion region of the third compartment is transmitted to the fourth compartment when the rotating second compartment is stopped with respect to the reference axis and delayed after a particular period of time. The separated first component located at the fourth compartment is outwardly transmitted by an acting force via the fourth compartment when the second compartment that was stopped and begins to rotate in a second direction different from the first direction with respect to the reference axis, so that the first component is completely separated from the second component.

The flow structure further comprises a fifth compartment communicated with the fourth compartment, wherein the separated first component located at the fourth compartment is outwardly transmitted to the fifth compartment by the acting force when the second compartment that was stopped and begins to rotate in the second direction different from the first direction with respect to the reference axis, so that the first component is completely separated from the second component.

The flow structure further comprises a first channel connected between the first compartment and the second compartment.

The flow structure further comprises a second channel connected between the second compartment and the third compartment. The second channel is radially distributed with respect to the reference axis. The second channel is a capillary channel. The first component of the tested specimen located at the second cushion region of the third compartment is automatically transmitted to the fourth compartment under a capillary function when the rotating second compartment is stopped. The second cushion region of the third compartment is a linear capillary channel. The fourth compartment is a linear capillary channel. The first cushion region and the second cushion region of the third compartment define a first angle. The first angle is not greater than 30 degrees. The second cushion region of the third compartment and the fourth compartment define a second angle. The second angle is not less than 90 degrees.

The flow structure further comprises a transitive channel disposed between the second cushion region of the third compartment and the fourth compartment. The second compartment and the first cushion region of the third compartment are radially distributed with respect to the reference axis.

The flow structure further comprises a sixth compartment communicated with the third compartment and the fourth compartment.

The flow structure further comprises a main body having a base surface. The first compartment, the second compartment, the first cushion region and the second cushion region of the third compartment and the fourth compartment comprise chamber structures which are formed together on the base surface of the main body. The depths of the chamber structures of the second cushion region of the third compartment and the fourth compartment are less than that of the first compartment and the first cushion region of the third compartment. The first cushion region of the third compartment comprises a first region communicated with the second compartment and a second region communicated with the first region, and a channel-depth difference is formed between the first compartment and the second compartment. A middle region is located between the first region and the second region, wherein channel-depth differences are respectively formed between the first region and the middle region and between the second region and the middle region, and the second cushion region is communicated with the middle region.

The acting force comprises a Coriolis force generated by Coriolis acceleration. The tested specimen is moved by an accelerating motion in the first predetermined period of time with respect to the reference axis. The tested specimen is moved by a uniform velocity motion in the second predetermined period of time with respect to the reference axis. A specific gravity of the first component is different from that of the second component.

Further, the invention provides an analytical system. The analytical system comprises a working fluid, a uniform dividing unit, a separation unit and a centrifugal chamber.

The working fluid comprises a first component and a second component with different characteristics. The uniform dividing unit relatively rotated with respect to a reference axis is utilized to uniformly divide the working fluid. The separation unit utilized to centrifugally separate the first and second components of the working fluid located at the uniform dividing unit comprises a centrifugal chamber and a separation channel. The centrifugal chamber comprising a first cushion region and a second cushion region connects to the first cushion region. The working fluid located at the uniform dividing unit is transmitted to the centrifugal chamber at a first predetermined period of time when the uniform dividing unit is rotated with respect to the reference axis in a first direction, and the separation of the first and second components of the working fluid located at the first cushion region of the centrifugal chamber is performed at a second predetermined period of time. The first predetermined period of time is prior to the second predetermined period of time, and the second cushion region of the centrifugal chamber is filled with the separated first component. The separation channel is communicated with the centrifugal chamber. The first component of the working fluid located at the first cushion region and the second cushion region of the centrifugal chamber is transmitted to the separation channel when the rotating uniform dividing unit is stopped with respect to the reference axis and delayed after a particular period of time, and the separated first component located at the separation channel is outwardly transmitted by an acting force via the separation channel when the uniform dividing unit that was stopped begins to rotate in a second direction different from the first direction with respect to the reference axis, so that the first component is completely separated from the second component.

The separation unit further comprises a detection chamber communicated with the separation channel, wherein the separated first component located at the separation channel is outwardly transmitted to the detection chamber by the acting force when the uniform dividing unit that was stopped begins to rotate in the second direction different from the first direction with respect to the reference axis, so that the first component is completely separated from the second component. A specific gravity of the first component is different from that of the second component. The working fluid is a blood, the first component is a plasma, and the second component is a blood cell.

The separation unit comprises a second channel connected between the uniform dividing unit and the centrifugal chamber. The second channel is radially distributed with respect to the reference axis. The second channel is a capillary channel. The first component of the working fluid located at the second cushion region of the centrifugal chamber is automatically transmitted to the separation channel under a capillary function when the rotating uniform dividing unit is stopped.

The second cushion region of the centrifugal chamber is a linear capillary channel. The separation channel is a linear capillary channel. The first cushion region and the second cushion region of the centrifugal chamber define a first angel which is not greater than 30 degrees. The second cushion region of the centrifugal chamber and the separation channel define a second angle which is not less than 90 degrees.

The separation unit further comprises a transitive channel disposed between the second cushion region of the centrifugal chamber and the separation channel. The uniform dividing unit and the first cushion region of the centrifugal chamber are radially distributed with respect to the reference axis.

The separation unit further comprises an exhaust slot communicated with the centrifugal chamber and the separation channel.

The analytical system further comprises a main body having a base surface. The uniform dividing unit, the first cushion region and the second cushion region of the centrifugal chamber and the separation channel comprise slotted structures which are formed together on the base surface of the main body.

The depths of the slotted structures of the second cushion region of the centrifugal chamber and the separation channel are less than that of the first compartment and the first cushion region of the centrifugal chamber.

The first cushion region of the centrifugal chamber comprises a first region communicated with the uniform dividing unit and a second region communicated with the first region, and a channel-depth difference is formed between the first compartment and the uniform dividing unit. The analytical system further comprises a middle region located between the first region and the second region, wherein channel-depth differences are respectively formed between the first region and the middle region and between the second region and the middle region, and the second cushion region is communicated with the middle region.

The acting force comprises a Coriolis force generated by Coriolis acceleration. The working fluid is moved by an accelerating motion in the first predetermined period of time with respect to the reference axis. The working fluid is moved by a uniform velocity motion in the second predetermined period of time with respect to the reference axis.

The analytical system further comprises a plurality of objects with a first marked substance and disposed in the uniform dividing unit, and the working fluid further comprises a second marked substance capable of bonding to the first marked substance of the objects.

The objects comprise glass balls, magnetic balls or other carriers. The first marked substance comprises a conjunctive DNA or RNA, a protein, a biomarker, an antibody, cell, or other biomoleculars. The second marked substance comprises a markable complementary DNA or RNA, a substrate, an enzyme, a coenzyme, a complement, an antigen, other cells or biomoleculars.

Additionally, the invention provides an analytical method. The analytical method comprises the steps of: providing a working fluid comprising a first component and a second component with different characteristics providing a uniform dividing unit relatively rotated with respect to a reference axis to uniformly divide the working fluid and providing a centrifugal chamber and a separation channel to centrifugally separate the first and second components of the working fluid located at the uniform dividing unit. The centrifugal chamber comprises a first cushion region and a second cushion region connecting to the first cushion region.

The working fluid located at the uniform dividing unit is transmitted to the centrifugal chamber at a first predetermined period of time when the uniform dividing unit is rotated with respect to the reference axis in a first direction, and the separation of the first and second components of the working fluid located at the first cushion region of the centrifugal chamber is performed at a second predetermined period of time. The first predetermined period of time is prior to the second predetermined period of time, and the second cushion region of the centrifugal chamber is filled with the separated first component. The separation channel is communicated with the centrifugal chamber. The first component of the working fluid located at the first cushion region and the second cushion region of the centrifugal chamber is transmitted to the separation channel when the rotating uniform dividing unit is stopped with respect to the reference axis and delayed after a particular period of time, and the separated first component located at the separation channel is outwardly transmitted by an acting force via the separation channel when the uniform dividing unit that was stopped begins to rotate in a second direction different from the first direction with respect to the reference axis, so that the first component is completely separated from the second component.

The analytical method further provides a detection chamber communicated with the separation channel, wherein the separated first component located at the separation channel is outwardly transmitted to the detection chamber by the acting force when the second compartment that was stopped, begins to rotate in the second direction different from the first direction with respect to the reference axis, so that the first component is completely separated from the second component.

The analytical method further provides a second channel connected between the second compartment and the centrifugal chamber. The second channel is radially distributed with respect to the reference axis. The first component of the working fluid located at the second cushion region of the centrifugal chamber is automatically transmitted to the separation channel under a capillary function when the rotating second compartment is stopped. The first cushion region and the second cushion region of the centrifugal chamber define a first angel which is not greater than 30 degrees. The second cushion region of the centrifugal chamber and the separation channel define a second angle is not less than 90 degrees.

The analytical method further comprises a transitive channel disposed between the second cushion region of the centrifugal chamber and the separation channel. The acting force comprises a Coriolis force generated by Coriolis acceleration. The working fluid is moved by an accelerating motion in the first predetermined period of time with respect to the reference axis. The working fluid is moved by a uniform velocity motion in the second predetermined period of time with respect to the reference axis. The analytical method further comprises a plurality of objects with a first marked substance and disposed in the uniform dividing unit, and the working fluid further comprises a second marked substance capable of bonding to the first marked substance of the objects. The first marked substance comprises a conjunctive DNA or RNA, a protein, a biomarker, an antibody, cell, or other biomoleculars. The second marked substance comprises a markable complementary DNA or RNA, a substrate, an enzyme, a coenzyme, a complement, an antigen, other cells or biomoleculars. A specific gravity of the first component is different from that of the second component.

Figure 1B:
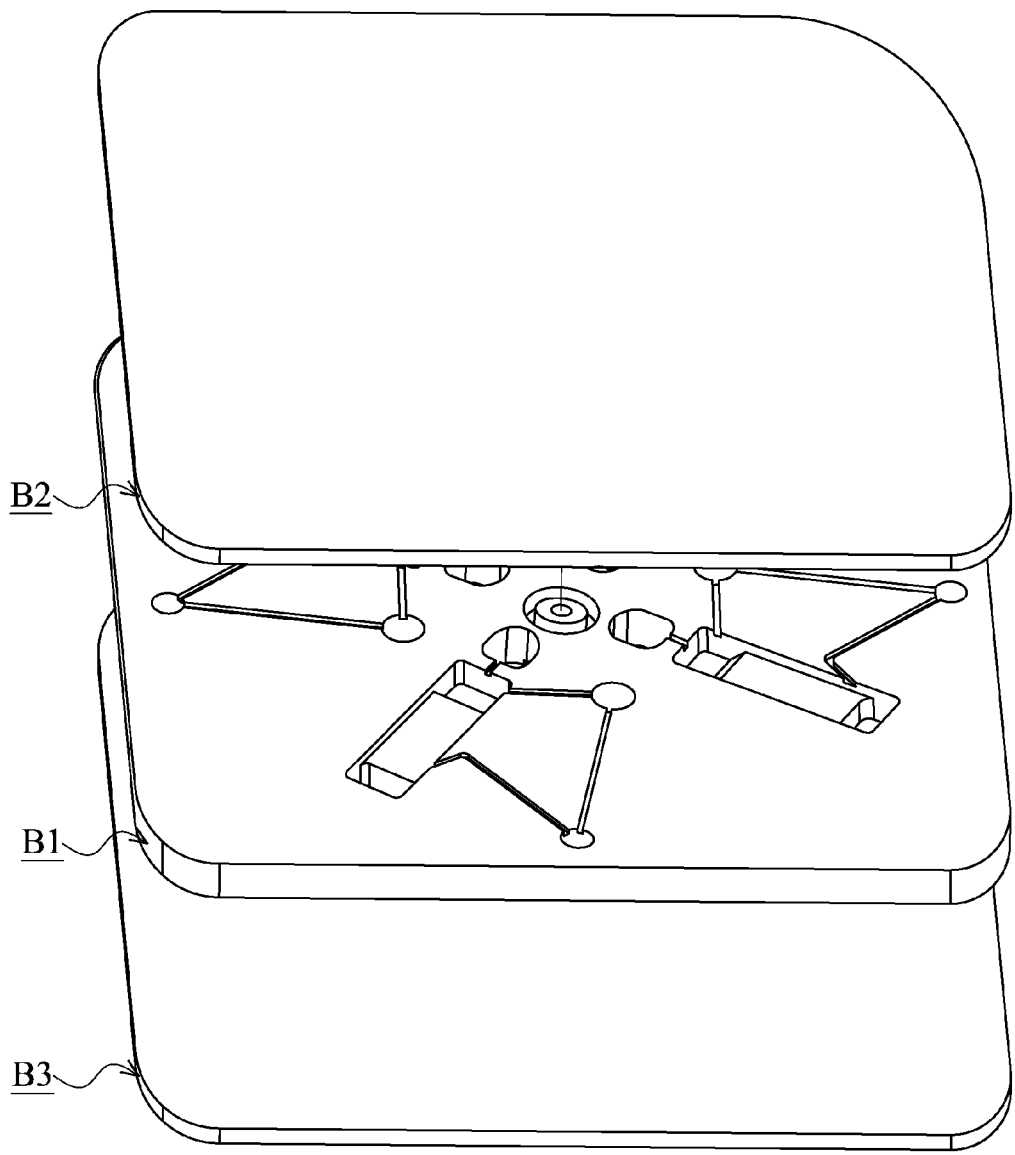
FIG. 1B is an exploded perspective view of the flow structure of FIG. 1A.

FIG. 1A is an assembled perspective view of a flow structure M of the embodiment, and FIG. 1B is an exploded perspective view of the flow structure M of FIG. 1A.

The flow structure M comprises a main body B1, an upper cover B2 and a lower cover B3. The main body B1 configured with flow paths is disposed between the upper cover B2 and the lower cover B3, and the flow paths of the main body B1 is covered by the upper cover B2. Thus, a closed space is formed between the main body B1 and the upper cover B2. In this embodiment, the upper cover B2 is a membrane utilized to bond to the main body B1 by packaging. The flow structure M of the embodiment is capable of performing uniform division and separation of a working fluid (e.g., a blood, a sample or a tested specimen) comprising several components with different characteristics (e.g. specific gravities), thereby performing analysis and detection of the working fluid.

Figure 2A:
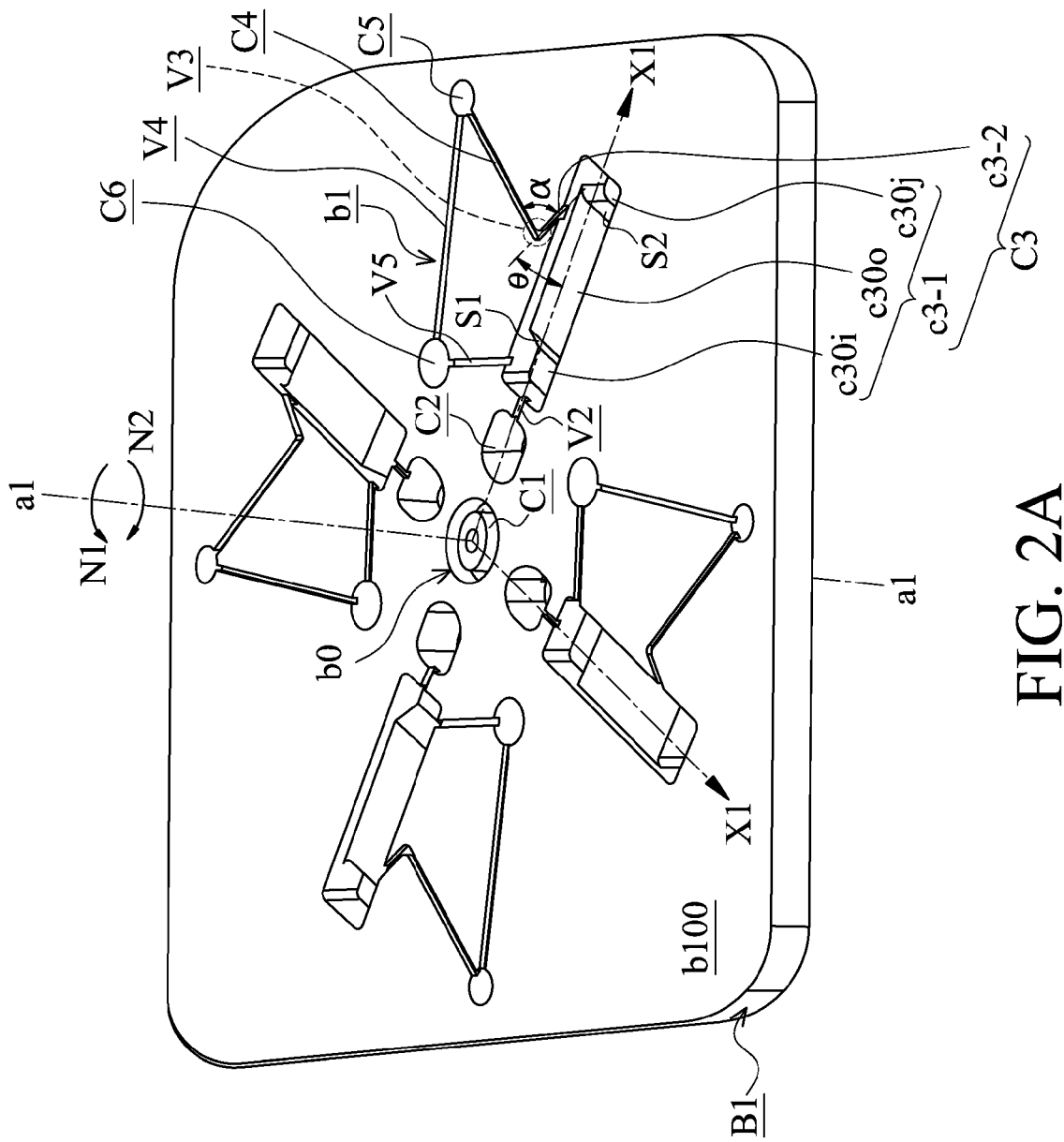
FIG. 2A is a perspective view of a main body of the flow structure of FIG. 1A.
Figure 2B:
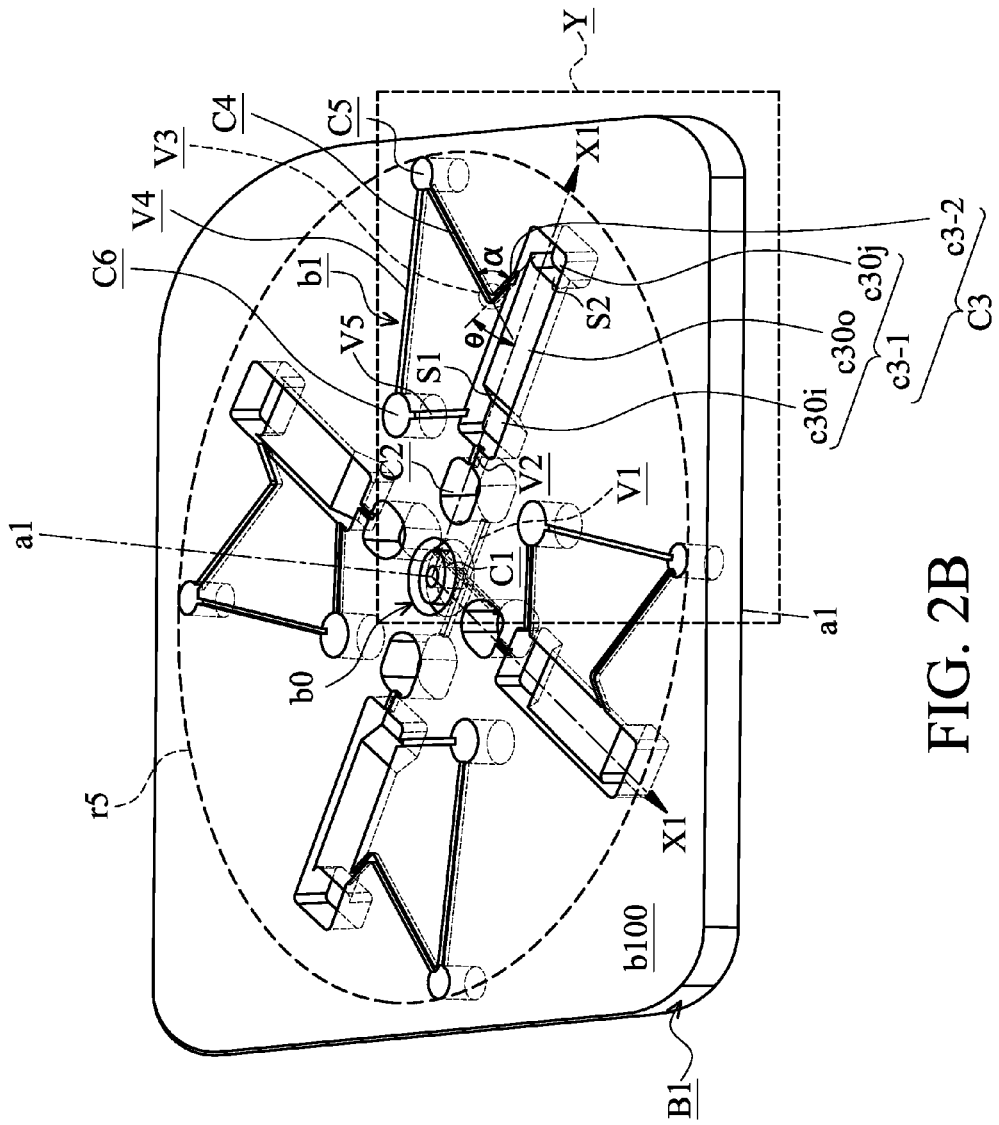
FIG. 2B is another perspective view of the main body of the flow structure of FIG. 1A.

FIG. 2A is a perspective view of a main body B1 of the flow structure M of FIG. 1B, and FIG. 2B is another perspective view of the main body B1 of the flow structure M of FIG. 1B. The main body B1 comprises a base surface b100, an injection hole b0, and a plurality of flow paths b1 communicated with the injection hole b0. The injection hole b0 and the flow paths b1 are disposed on the base surface b100. A reference axis a1-a1 is configured to define the location of the injection hole b0. The flow paths b1, equally spaced from each other and centrally disposed with respect to or relative to the reference axis a1-a1, are symmetrically and radially distributed along radial directions X1, respectively. The main body B1 is rotated with respect to the reference axis a1-a1 in a first direction N1 or a second direction N2. In this embodiment, the amount of the flow paths b1 is four.

Although the four flow paths b1 are symmetrically formed as well as the injection hole b0 and the flow paths b1 are disposed on the same plane base surface b100, all is not limited thereto. The amount of the flow paths b1 and the location of the injection hole b0 and the flow paths b1 can have various modifications and similar arrangements, as long as the uniform division and separation of the working fluid can be achieved. To briefly describe the structure of the main body B1, a single flow path b1 is utilized.

The flow path b1 comprises a first compartment C1, a second compartment C2, a third compartment C3, a fourth compartment C4, a fifth compartment C5, a sixth compartment C6, a first channel V1 (see FIG. 2B), a second channel V2, a transitive channel V3 and two exhaust channels V4/V5. The first compartment C1, the second compartment C2, the third compartment C3, the fourth compartment C4, the fifth compartment C5, the sixth compartment C6, the first channel V1, the second channel V2, the transitive channel V3 and the exhaust channels V4/V5 are slotted structures which are formed together on the base surface b100 of the main body B1. More specifically, each of the flow paths b1 comprises a first path portion and a second path portion. The first path portion located at the reference axis a1-a1 is an upstream section comprising the first compartment C1 and the second compartment C2 communicated with the first compartment C1 via the first channel V1. The second path portion is a downstream section formed as a looped path communicated with the second compartment C2 of the first path portion, comprising the third compartment C3, the transitive channel V3, the fourth compartment C4, the fifth compartment C5, the exhaust channel V4, the sixth compartment C6 and the exhaust channel V5. That is, the looped path, formed by the third compartment C3, the transitive channel V3, the fourth compartment C4, the fifth compartment C5, the exhaust channel V4, the sixth compartment C6 and the exhaust channel V5, does not directly communicated back to the first compartment C1. By taking the reference axis a1-a1 to form a dotted circle denoted by a reference numeral r5, it is understood that the fifth compartment C5 is arranged as an outermost compartment relative to the first compartment C1, the second compartment C2, the third compartment C3 and the fourth compartment C4.

In one embodiment, the upper cover B2 is removed before the analytical system is used, thereby connecting the first compartment C1 and the sixth compartment C6 to the atmospheric surrounding. Note that the first compartment C1 is a specimen injection hole, and the sixth compartment C6 is an exhaust hole.

With respect to the function of the flow paths b1 of the main body B1 of the flow structure M, each flow path b1 mainly comprises a uniform dividing unit W1, a separation unit W2, an exhaust unit W3 and a detection unit W4.

The uniform dividing unit W1 comprises the first compartment C1, the second compartment C2, the first channel V1 and the second channel V2.

In one embodiment, the first compartment C1 is an annular chamber structure disposed on the base surface b100, thereby forming the first compartment C1 as a receiving room for the injection hole b0. The second compartment C2 is a uniformly dividing chamber radially distributed along radial directions X1 and disposed on the base surface b100 with respect to the reference axis a1-a1. The first channel V1 is a hollow portion disposed between the bottom of the first compartment C1 and the bottom of the second compartment C2, thereby connecting the first compartment C1 to the second compartment C2. The second channel V2 is a linear capillary channel or slotted structure radially distributed along radial directions X1 and disposed on the base surface b100 with respect to the reference axis a1-a1 and communicated with the second compartment C2, i.e., the second compartment C2 serves as a check valve or capillary valve. That is to say, the depth of the second channel V2 is far less than that of the second compartment C2.

The separation unit W2 comprises the third compartment C3, the transitive channel V3 and the fourth compartment C4.

The third compartment C3 is a centrifugal chamber radially distributed along radial directions X1 and disposed on the base surface b100 with respect to the reference axis a1-a1. One side of the third compartment C3 is communicated with the second channel V2 of the uniform dividing unit W1, i.e., the second channel V2 is disposed between the second compartment C2 and the third compartment C3. The third compartment C3 comprises a first cushion region c3-1 and a second cushion region c3-2 communicated with the first cushion region c3-1. With respect to the base surface b100, the first cushion region c3-1 is a straight slotted structure comprising a first region c30$i$, a second region c30$j$, and a middle region c30$o$ connectively located between the first region c30$i$ and the second region c30$j$.

Figure 3:
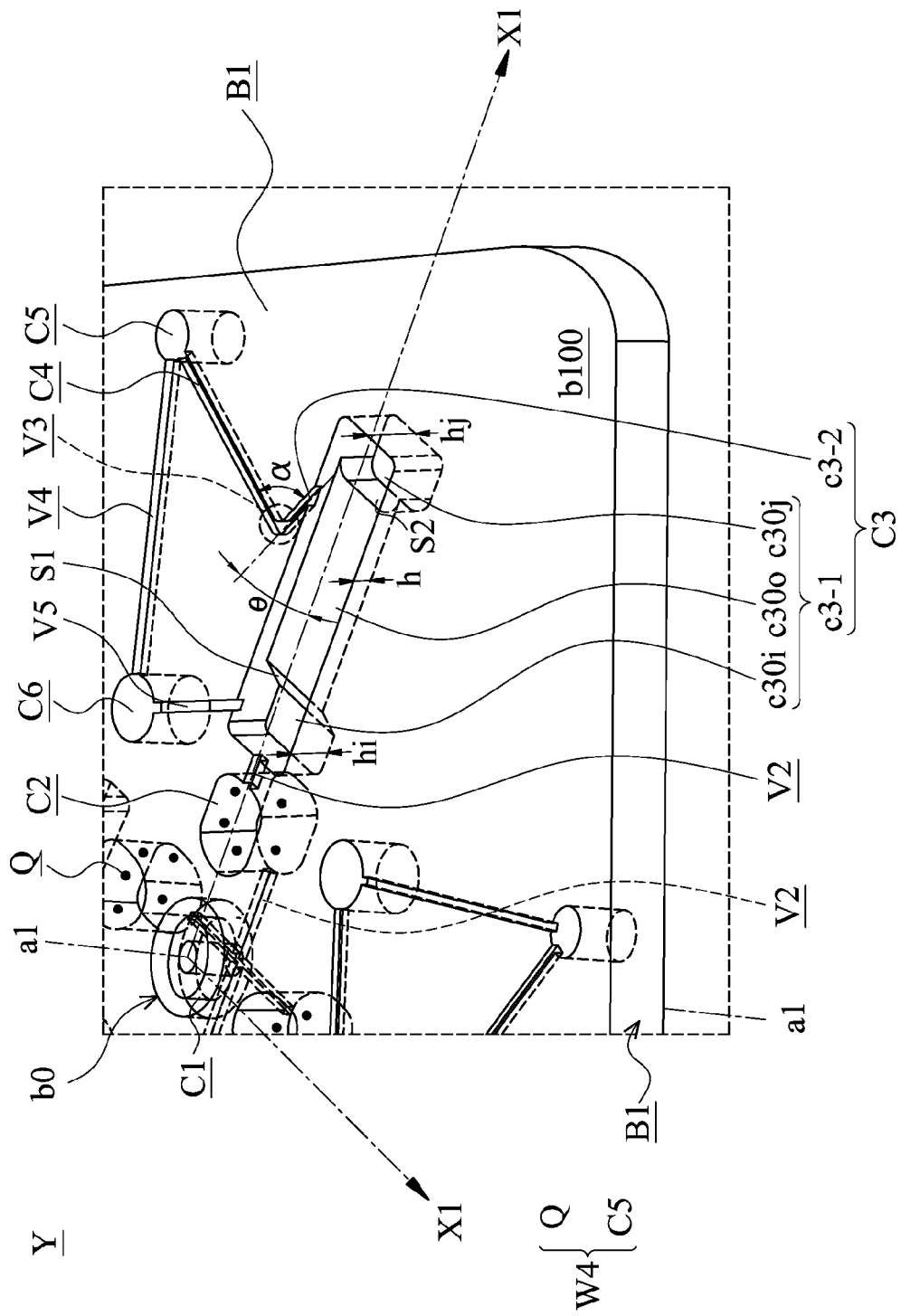
FIG. 3 is a partially enlarged view of a single flow path of the flow structure of zone (Y) in FIG. 2B.

Referring to FIGS. 2B and 3, the first region c30$i$, the middle region c30$o$ and the second region c30$j$ of the first cushion region c3-1 of the third compartment C3 have depths hi, h and hj, respectively. A difference hi-h is formed between the depth hi of the first region c30$i$ and the depth h of the middle region c30$o$. Another difference hj-h is formed between the depth hj of the second region c30$j$ and the depth h of the middle region c30$o$. The first region c30$i$ constitutes an upstream section of the centrifugal chamber to connect to the second channel V2, the second region c30$j$ constitutes the downstream section of the centrifugal chamber, and the middle region c30$o$ located between the first region c30$i$ and the second region c30$j$ connects to the second cushion region c3-2. With respect to the base surface b100, a slanted surface S1 is formed between the first region c30$i$ and the middle region c30$o$, and a perpendicular surface S2 is formed between the second region c30$j$ and the middle region c30$o$.

The second cushion region c3-2 of the third compartment C3 is a linear capillary channel disposed on the base surface b100 and communicated with the middle region c30$o$ of the first cushion region c3-1. That is to say, the depth of the second cushion region c3-2 is far less than the depth hi of the first region c30$i$, the depth h of the middle region c30$o$ or the depth hj of the second region c30$j$. The channel extended direction (radial direction X1) of the first cushion region c3-1 and the extended direction of the second cushion region c3-2 define a first angle θ which is preferably not greater than 30 degrees. In this embodiment, the first angle θ is 23 degrees. When the working fluid is injected into the first compartment C1, probability of blocking the working fluid by the capillary valve is high via the main body B1.

Figure 2C:
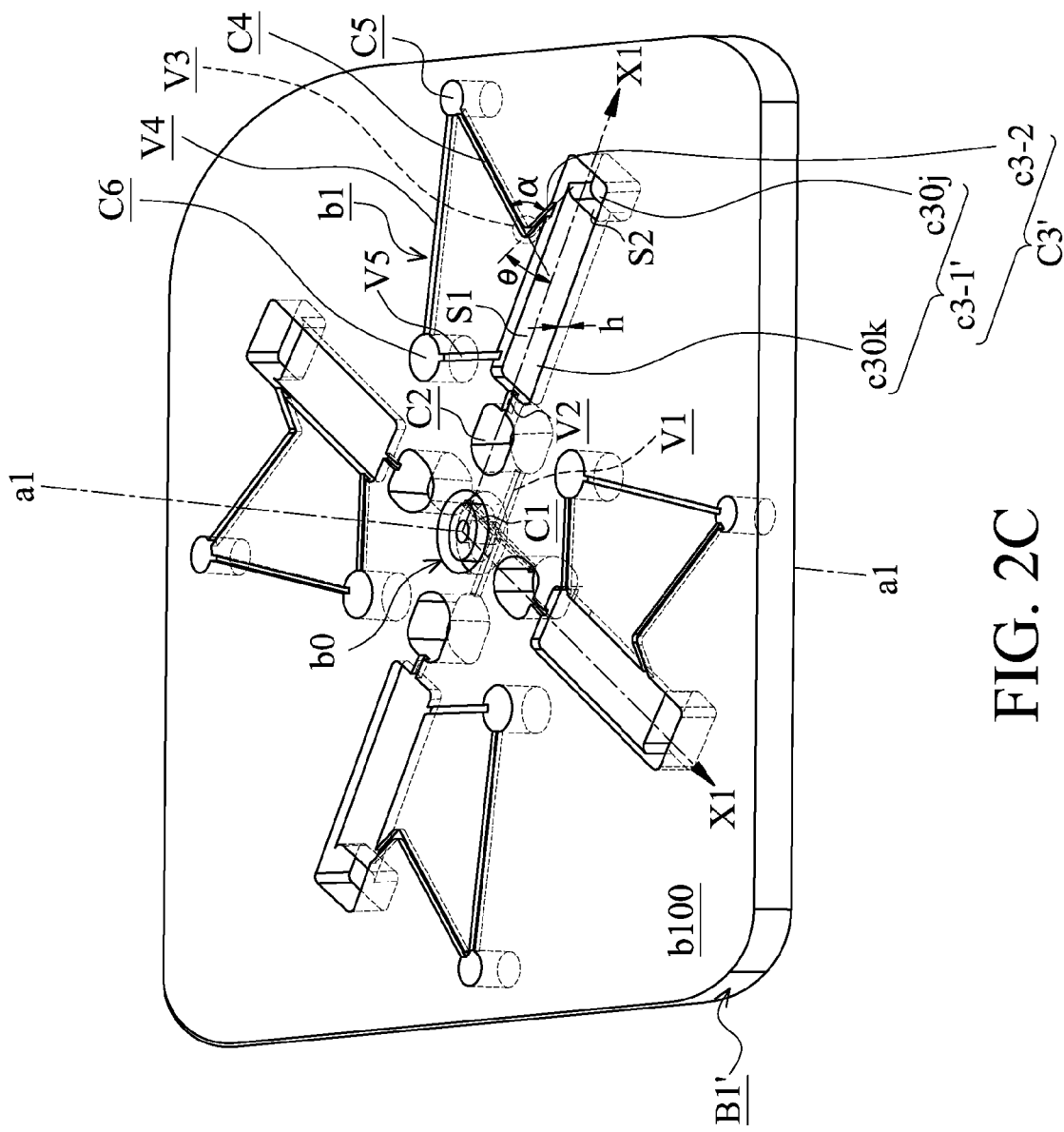
FIG. 2C is a perspective view of another main body of the flow structure of the invention.

FIG. 2C is a perspective view of another main body B1'. The main body B1' differs from the three connected regions, i.e., the first region c30$i$, the second region c30$j$ and the middle region c30$o$ of the main body B1, in that a first cushion region c3-1' of the main body B1' is a straight slotted structure formed by two connected regions, i.e., the first region c30$i$ and the middle region c30$o$ of the described embodiment are formed into a combined region c30$k$ with a depth h, thereby forming the first cushion region c3-1' of the third compartment C3' of the main body B1' by the combined region c30$k$ and the second region c30$j$. When the working fluid is injected into the first compartment C1, probability of blocking the working fluid by the capillary valve is high via the main body B1'.

The transitive channel V3 is a V-shaped capillary channel or slotted structure disposed on the base surface b100 and connected between the second cushion region c3-2 of the third compartment C3 and the fourth compartment C4. The fourth compartment C4 is a linear capillary dividing channel or slotted structure disposed on the base surface b100. That is, the transitive channel V3 and the fourth compartment C4 having same depth is formed into a continuous capillary channel or slotted structure, but the depths of the transitive channel V3 and the fourth compartment C4 is far less than the depth hi of the first region c30$i$, the depth h of the middle region c30$o$ or the depth hj of the second region c30$j$. Note that the extended directions of the fourth compartment C4 and the second cushion region c3-2 define a second angle α which is preferably not less than 90 degrees. In this embodiment, the second angle α is about 95 degrees. That is, the first cushion region c3-1 of the third compartment C3 is extended outwards relative to the reference axis a1-a1, the second cushion region c3-2 of the third compartment C3 is substantially extended inwards relative to the reference axis a1-a1, and the first cushion region c3-1 and the second cushion region c3-2 of the third compartment C3 form a first V-shaped path. The second cushion region c3-2 of the third compartment C3, the transitive channel V3 and the fourth compartment C4 form a second V-shaped path geometrically overlapped with the first V-shaped path formed by the first cushion region c3-1 and the second cushion region c3-2 of the third compartment C3, such that the first cushion region c3-1 and the second cushion region c3-2 of the third compartment C3, the transitive channel V3 and the fourth compartment C4 define a switchback structure.

Based on the described structure, it is understood that the second cushion region c3-2 of the third compartment C3, the transitive channel V3 and the fourth compartment C4 are formed into a continuous capillary channel with single depth, wherein the second cushion region c3-2 of the third compartment (centrifugal chamber) C3 and the fourth compartment (separation channel) C4 constitute a first section and second section of the continuous capillary channel, respectively.

Referring FIG. 3, FIG. 3 is a partially enlarged view of a single flow path b1 of the flow structure M of zone Y in FIG. 2B.

The detection unit W4 comprises the fifth compartment C5 and a plurality of objects Q with a first marked substance. The objects Q are selectively disposed in the second compartment C2. The fifth compartment C5 is a cylindrical detection chamber disposed on the base surface b100 and communicated with the separation channel C4. In this embodiment, the objects Q are glass balls or glass micro-balls with diameter ranging from 200 to 1000 micrometer (μm), and the first marked substance of the objects Q are a conjunctive DNA or RNA, a protein, a biomarker, an antibody, cell, or other biomoleculars. Additionally, it is noted that the glass balls are formed by a pre-treatment process (e.g., physical or chemical method is contained) with a single step or multiple steps, so that the function of catching particular targets can be achieved. A covering thin film is formed on the surfaces of the glass balls by a physical method (e.g., heated under high temperature, absorbed or deposited) or chemical method (e.g., amination (—HH2), hydrogenation (—OH), corboxyl group (—COOH) and aldehyde group (—CHO), etc.). Additionally, in other embodiments, the detection unit can be included by the separation unit, and the objects can be magnetic balls, physical carriers or other structs.

The exhaust unit W3 comprises the exhaust channels V4/V5 and the exhaust chamber C6. The exhaust channel V4 is a linear capillary channel or slotted structure disposed on the base surface b100 and communicated with the fifth compartment C5. The exhaust chamber C6 is a cylindrical exhaust chamber disposed on the base surface b100 and communicated with the exhaust channel V4. The exhaust channel V5 is a linear capillary channel or slotted structure disposed on the base surface b100 and disposed connectively between the exhaust chamber C6 and the first cushion region c3-1 of the third compartment C3. In the embodiment of FIG. 2C, the exhaust channel V5 is disposed connectively between the exhaust chamber C6 and the combined region c30k of first cushion region c3-1' of the third compartment C3'. That is to say, the depths of the exhaust channels V4/V5 are far less than that of the fifth compartment C5 or the exhaust chamber C6.

Figure 4:
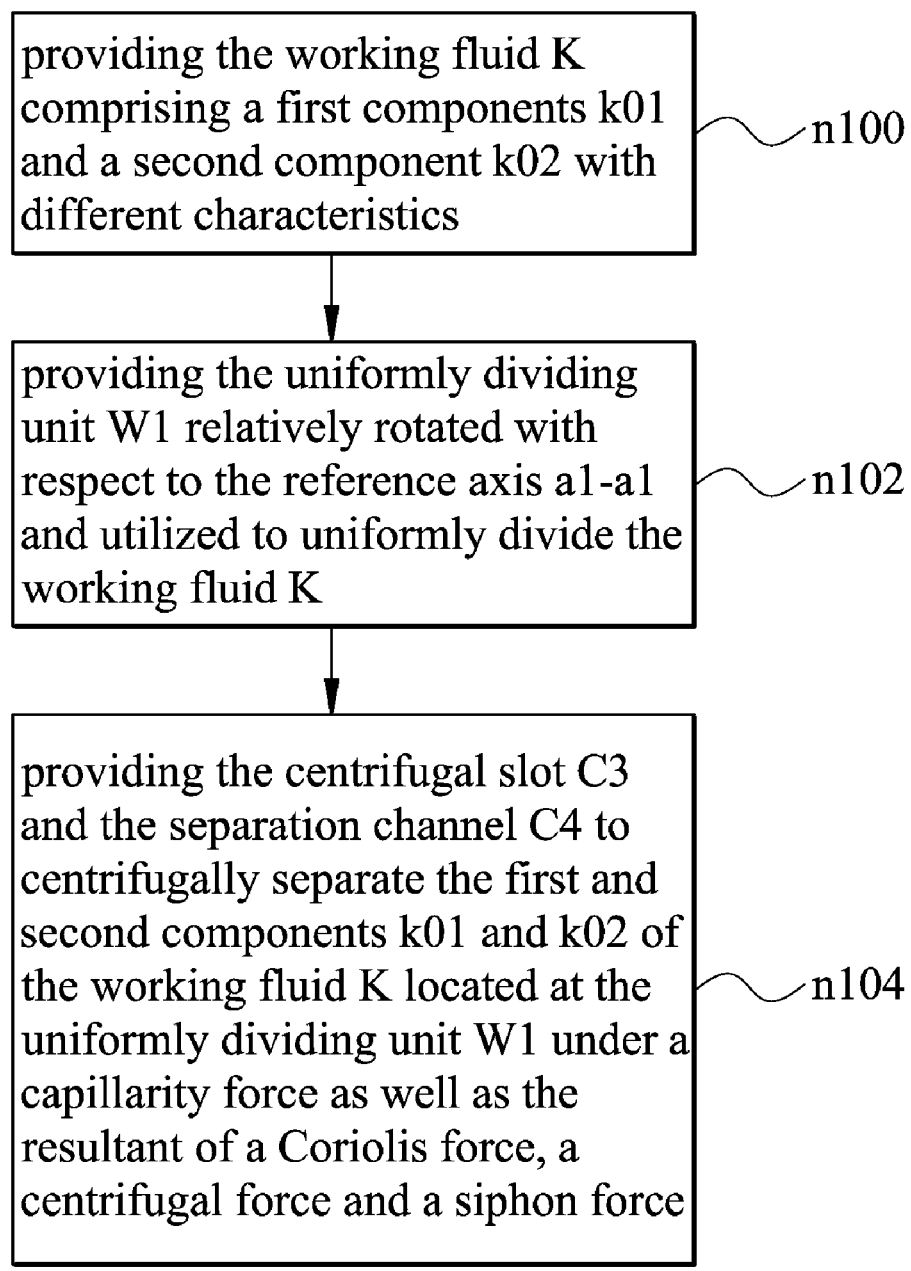
FIG. 4 is an operation flow chart of an analytical system of the invention.

FIG. 4 is an operation flow chart of an analytical system Z. The analytical method comprises the steps of: providing the working fluid K comprising a first component k01 and a second component k02 with different characteristics (step n100); providing the uniform dividing unit W1 to uniformly divide the working fluid K (step n102), which is relatively rotated with respect to the reference axis a1-a1; and providing the centrifugal chamber C3 and the separation channel C4 to centrifugally separate the first and second components k01 and k02 of the working fluid K located at the uniform dividing unit W1 under a capillarity force as well as the result of a Coriolis force, a centrifugal force and a siphon force (step n104).

Figure 5A:
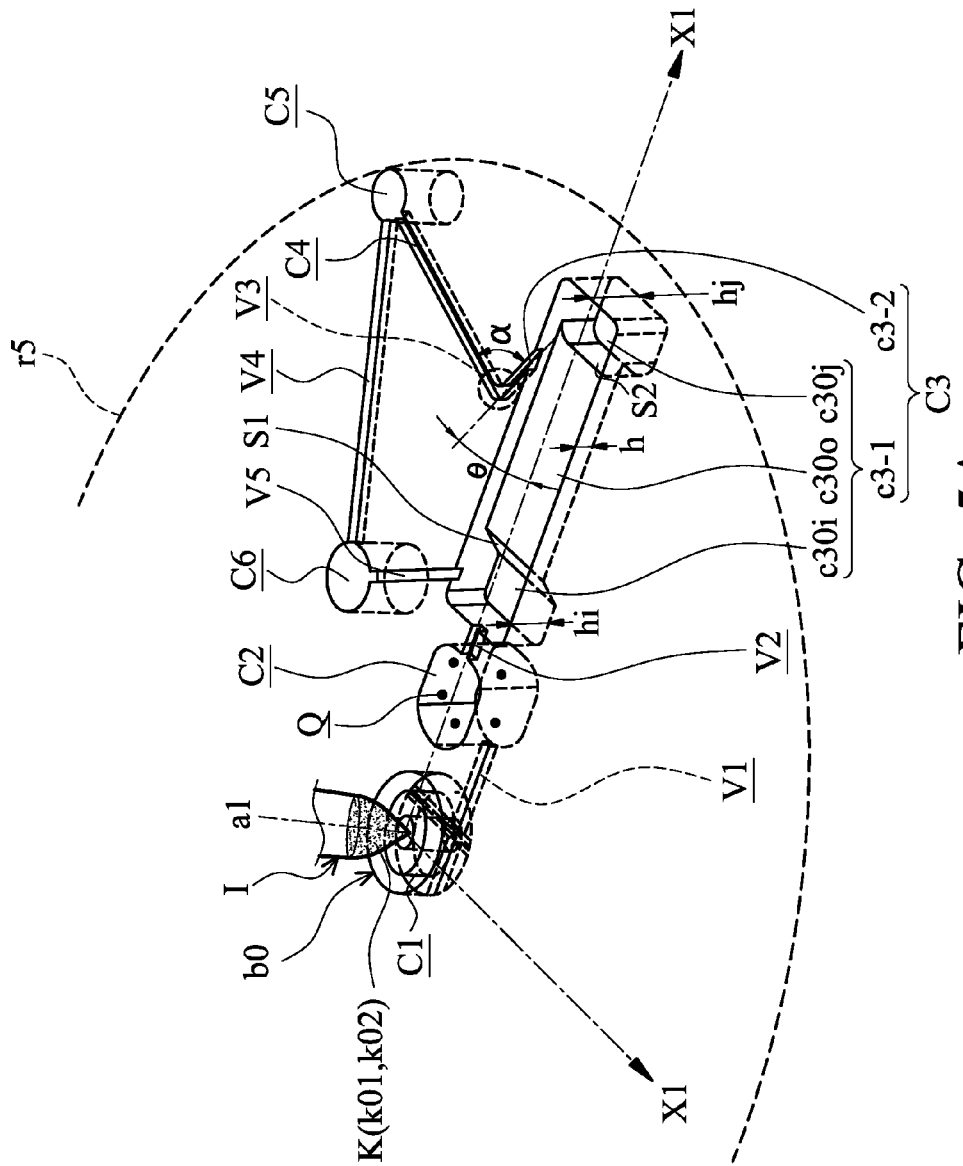
FIG. 5A is a schematic view of a tested specimen transmitted to a first compartment of the single flow path.
Figure 5B:
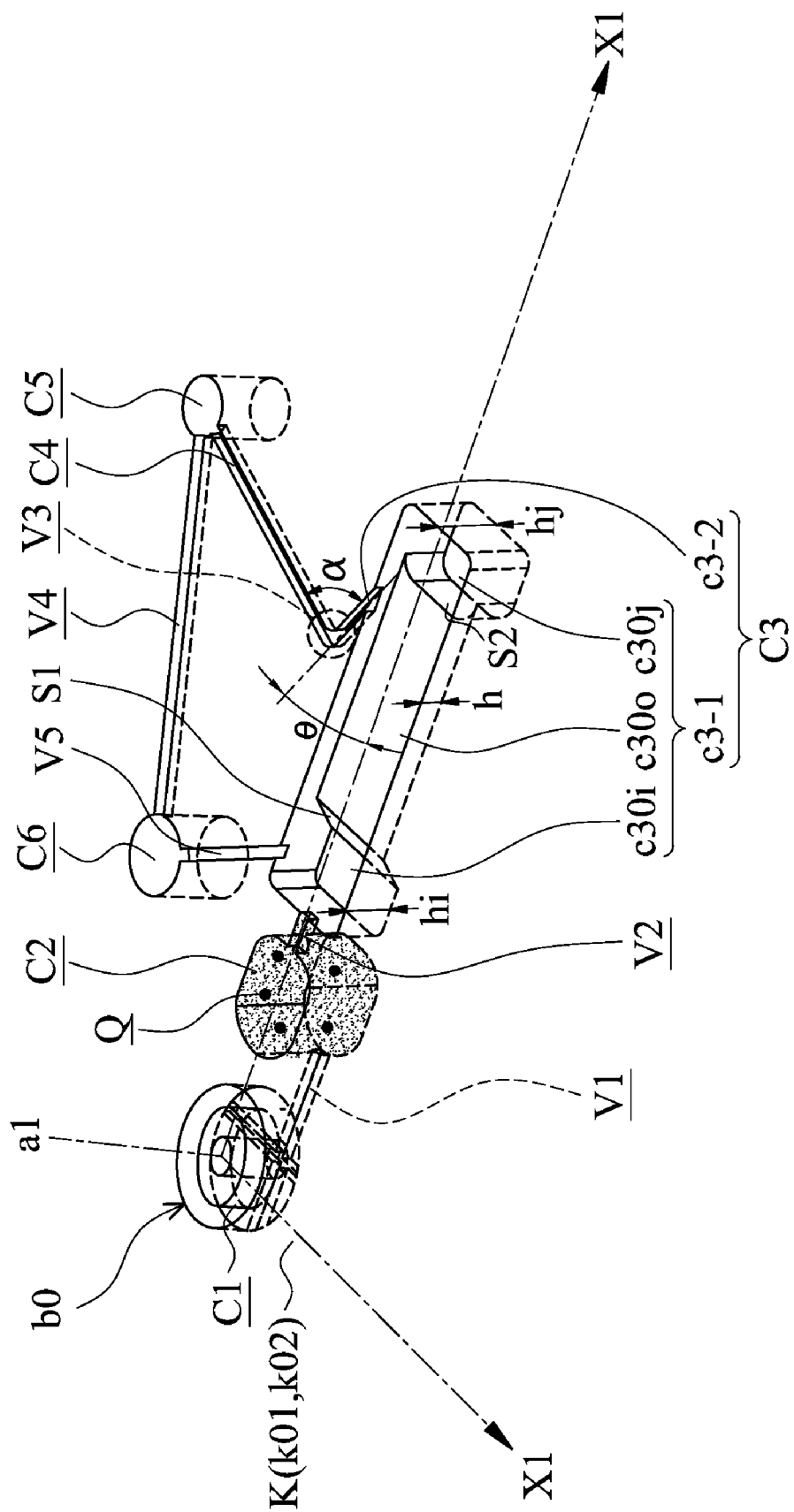
FIG. 5B is a schematic view of part of the tested specimen located at the first compartment to be transmitted to a second compartment after a division process.

FIGS. 5A to 5F are schematic views showing the operation of the analytical system Z. FIG. 5A is a schematic view of a tested specimen K transmitted to the first compartment C1 of the flow path b1 through the injection hole b0 and the main body B1 of the flow structure M by a sampler T, e.g., a pipette with a tip. In this embodiment, the predetermined volume of the tested specimen K received in the sampler T is about 50 μl. FIG. 5B is a schematic view of part of the tested specimen K located at the first compartment C1 to be uniformly divided and transmitted to the second compartment C2 after the division process. The working fluid K comprises a first component k01 and a second component k02 with different characteristics. For example, a specific gravity of the first component k01 is different from that of the second component k02. In this embodiment, the working fluid K is a blood, the first component k01 is a plasma, and the second component k02 is a blood cell or haemocyte having specific gravity greater than that of the blood. In FIG. 5A, the objects Q are selectively disposed in the second compartment C2 of the uniform dividing unit W1, thereby detecting the working fluid K.

When the working fluid K received in the sampler T is transmitted to the first compartment C1 via the injection hole b0 of the main body B1, the working fluid K is only filled in the first channels V1, the second compartments C2 and the second channel V2 of the uniform dividing unit W1 due to the limitation of the capillary structure of the second channel V2. That is, the working fluid K is uniformly divided and transmitted to the second compartments C2, and the working fluid K does not enter the third compartment C3 of the separation unit W2.

In addition to using the pipette which is capable of injecting the tested specimen K and quantitatively retrieving the tested specimen K before injection, a capillary pipe (not shown in FIGS.) can also be adopted. The capillary pipe can directly sample the tested specimen K to be inserted into the center of a test strip, thus, the working fluid located in the capillary pipe can be automatically transmitted to each dividing chamber by an amphipathic film effect.

The working fluid K comprises a second marked substance which can be a markable complementary DNA or RNA, a substrate, an enzyme, a coenzyme, a complement, an antigen, other cells or biomoleculars. When the working fluid K and the objects Q located in the second compartment C2 are motionlessly placed and reacted for a predetermined period of time, the second marked substance of the working fluid K is bonded to the first marked substance of the objects Q by the connection of targets, thus, forming bio composites BIO-CO (see FIG. 6B).

Figure 5C:
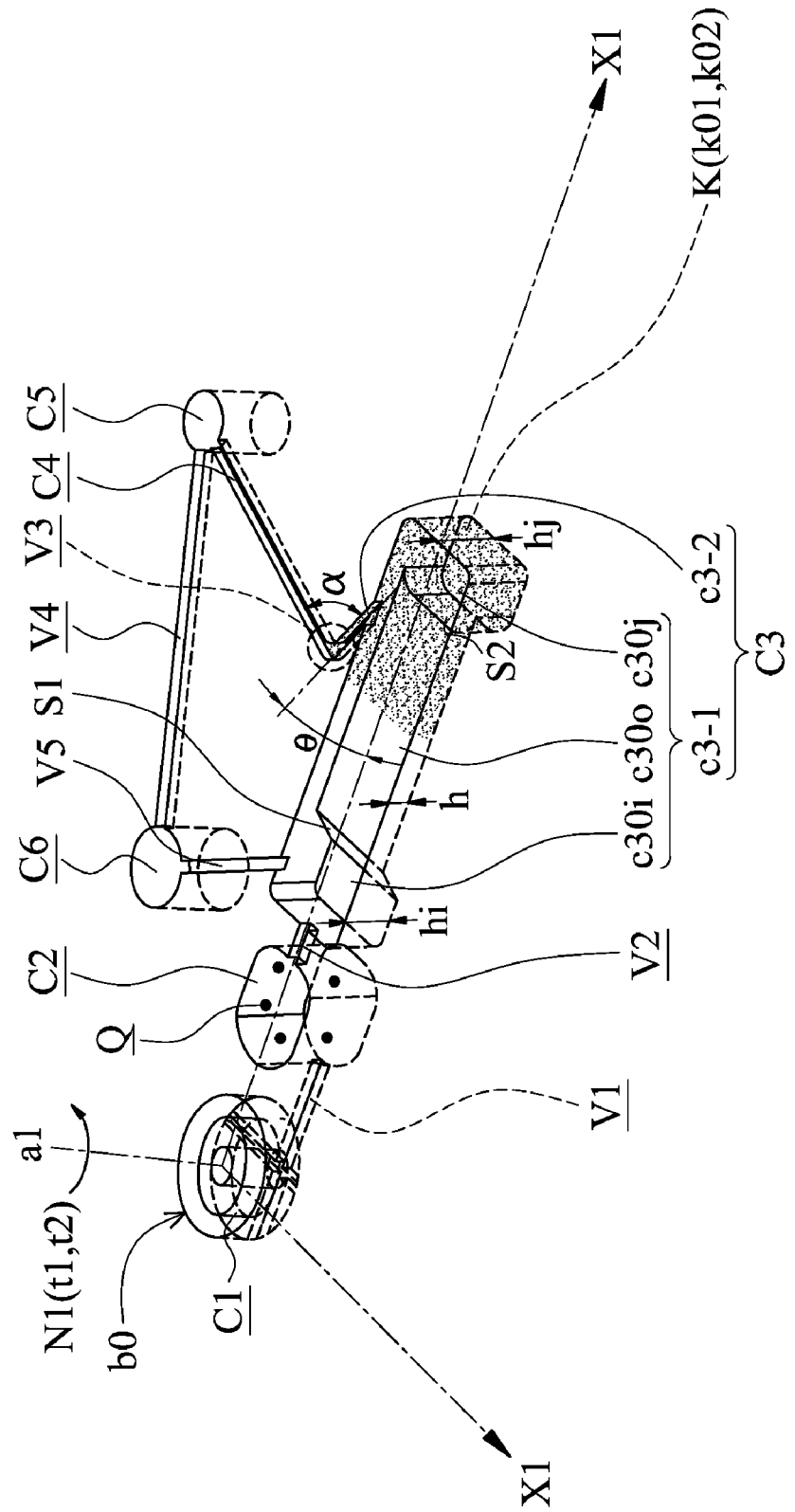
FIG. 5C is a schematic view of the main body of the flow structure rotated about a first direction with respect to a reference axis.

FIG. 5C is a schematic view of the main body B1 of the flow structure M rotated in a first direction N1 with respect to a reference axis a1-a1. When the uniform dividing unit W1 is rotated with respect to the reference axis a1-a1 in the first direction N1, the working fluid K located at the uniform dividing unit W1 is transmitted to the first and second cushion regions c3-1 and c3-2 of the centrifugal chamber C3 at a first predetermined period of time t1, and the separation of the first and second components k01 and k02 of the working fluid K located at the first cushion region c3-1 of the centrifugal chamber C3 is performed at a second predetermined period of time t2, wherein the first predetermined period of time t1 is prior to the second predetermined period of time t2, and the second cushion region c3-2 of the centrifugal chamber C3 is filled with the separated first component k01. In this embodiment, the first direction N1 is a counter clockwise (CCW) direction, the rotational speed is designed as 4,000 RPM, the rotation of the first predetermined period of time t1 includes a first step (pre-step) for performing an acceleration motion (run time: 0 to 5 second, speed: 0-4,000 rpm), and the second predetermined period of time t2 includes a second step (post-step) for performing a uniform velocity motion (run time: 5 to 60 sec, speed: 4,000 rpm).

When the acceleration motion of the first step is performed (run time: 0 to 5 sec, speed: from 0 to 4,000 rpm), a centrifugal force under high rotation speed drives the working fluid K located in the second compartment C2 to flow through the second channel V2 to attain the first and second cushion regions c3-1 and c3-2 of the centrifugal chamber C3.

When the uniform velocity motion of the second step is performed (run time t2: from 5 to 60 sec, speed: 4,000 rpm), the second component k02 having the specific gravity greater than that of the first component k01 is kept at the bottom of the second region c30j of the first cushion region c3-1 of the third compartment C3 under the centrifugal force of rotation, the separated first component k01 is kept at the top of the second region c30j of the first cushion region c3-1 of the third compartment C3 and the middle region c30o, and the separated first component k01 is also kept at the transitive channel V3 by the centrifugal force.

Figure 5D:
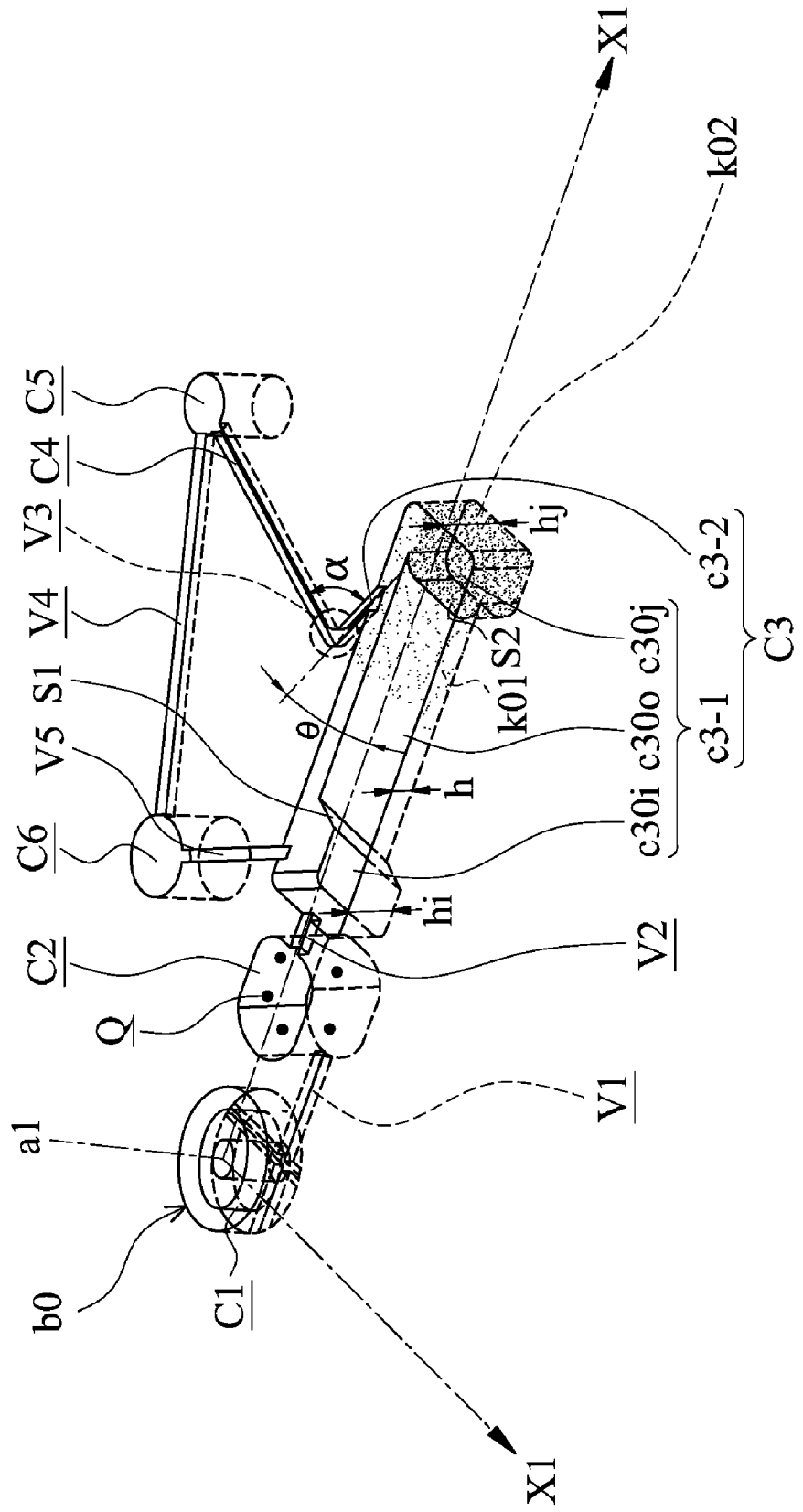
FIG. 5D is a schematic view of a separated first component being transmitted to a fourth compartment when the main body of the flow structure of FIG. 5C is stopped and delayed after a particular period.

FIG. 5D is a schematic view of the separated first component k01 being transmitted to the fourth compartment C4 when the main body B1 of the flow structure M of FIG. 5C is stopped and delayed after a particular period of time. Because of a capillary function formed between the second cushion region c3-2 of the centrifugal chamber C3, the fourth compartment C4 and the separated first component k01 located in the transitive channel V3, the first component k01 of the working fluid K located at the second cushion region c3-2 of the centrifugal chamber C3 is transmitted to the separation channel C4 when the rotating uniform dividing unit W1 is stopped and delayed after a particular period of time.

Figure 5E:
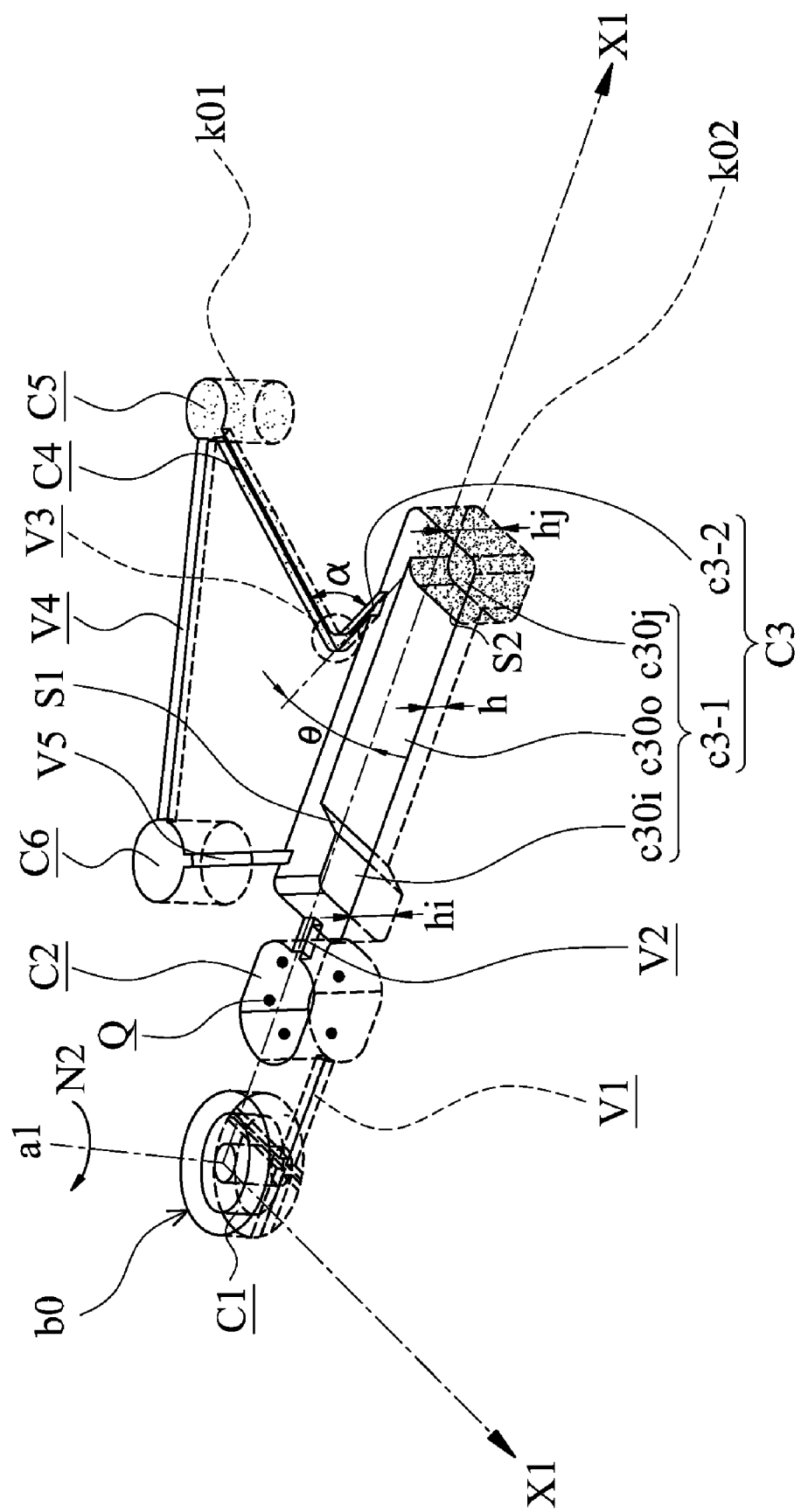
FIG. 5E is a schematic view of the separated first component being transmitted to a fifth compartment via the fourth compartment when the main body of the flow structure that was stopped of FIG. 5D begins to rotate in a second direction with respect to the reference axis.

FIG. 5E is a schematic view of the main body B1 of the flow structure M that was stopped of FIG. 5D, beginning to rotate in a second direction N2 at a low velocity with respect to the reference axis a1-a1, wherein the second direction N2 is different from the first direction N1. In this embodiment, the second direction N2 is a clockwise (CW) direction opposite to the first direction N1.

When the main body B1 that was stopped begins to rotate in the second direction N2 at a low velocity (speed: 2,000 to 2,500 rpm, run time: 5 to 15 sec) with respect to the reference axis a1-a1, the separated first component k01 located at the fourth compartment C4 is outwardly transmitted under an acting force which is the resultant force of the Coriolis force and the siphon force, thereby to completely separate the first component k01 from the second component k02 and to be filled in the fifth compartment C5 of the detection unit W4. Further, the first component k01 located in the fifth compartment C5 can be reacted with a reaction reagent (not shown in FIGS.) preset in the fifth compartment C5.

In another embodiment where the reaction reagent is not preset in the fifth compartment C5, when the first component k01 is completely separated from the second component k02 and filled in the fifth compartment C5 of the detection unit W4, the separation process of the analytical system is finished. It is necessary to check whether the color of the first component k01 located in the fifth compartment C5 is transparent yellow or not and whether the tested blood (e.g., the working fluid K) is hemolytic or not. If the color of the first component k01 located in the fifth compartment C5 is red, the tested blood specimen fails the test, i.e., the tested blood is hemolytic and not suitable for being a specimen of a cartridge testing, and the described sampling process must be repeated.

According to the locations of all chamber structures, it is known that the location of the fifth compartment C5 of the detection unit W4 has a maximum rotational radius with respect to the reference axis a1-a1, thereby increasing the stability of the reagent located in the fifth compartment C5 of the detection unit W4. In the described steps of the analytical method, the division process and the separation process can be normally operated when gases from all slotted structures are expelled by the exhaust channel V4 of the exhaust unit W3, the sixth compartment C6 and the exhaust channel V5. Further, the division/separation processes and the exhaust process of the uniform dividing unit W1 and the separation unit W2 are simultaneously operated, so that the division/separation processes thereof can be normally operated.

The related applications of the analytical system Z and the flow structure M thereof are described below.

In FIG. 5B, when the tested specimen K (blood) located in the second compartment C2 (uniformly dividing chamber) of the flow structure M are motionlessly placed and reacted for the predetermined period of time, the objects Q (glass micro-balls) located in the second compartment C2 (uniformly dividing chamber), the tested targets and the markable biomoleculars (second marked substance) are bonded. In a fluorescent detection process, the first biomoleculars are capable of bonding with the second biomoleculars having chromophore by the tested target molecular, and a fluorescent signal can be read from the fifth compartment C5 (detection chamber). In a cold-light or light-absorbed detection process, after the first biomoleculars are bonded to the second biomoleculars via the target to be tested, the bonded first and second biomoleculars located in the fifth compartment C5 (detection chamber) can be reacted with the added substrates SUB, thus, a cold-light or light-absorbed optical signal or luminous product L can be obtained.

By bonding the first biomolecular to the second biomolecular via the target to be tested, the bio composite BIO-CO is formed (see FIG. 6B), and the other non targets (non-TA) to be tested (see FIGS. 6A and 6B) having no reaction thereof is suspended in the working fluid. When the flow structure M disposed on a systematic rotating table (not shown in FIGS.) is rotated at a high speed about the injection hole b0 thereof, the tested specimen K (blood) passes through the second channel V2 (check valve), and the first component k01 (plasma) and the second component k02 (blood cell) are centrifugally separated into different layers due to different specific gravities, thus, the second component k02 (blood cell) is accumulated at the lower side of the third compartment C3 (centrifugal chamber) and the first component k01 (plasma) is accumulated at the upper side of the third compartment C3 (centrifugal chamber).

Because the volume of the object Q (glass micro-ball) bonded to the tested target is greater than the pore size of the second channel V2 (check valve), the objects Q (glass micro-balls) are blocked and kept in the third compartment C3 (centrifugal chamber), and the other non-bonded luminous dyes accompanied with the first component k01 (plasma) flow to the lower side of the third compartment C3 (centrifugal chamber). With the capillary force of miniature flow path, the first component k01 (plasma) sequentially passes through the transitive channel V3 and flows to the fifth compartment C5 (detection chamber) communicated with the rear end of the separation channel C4.

Figure 6A:
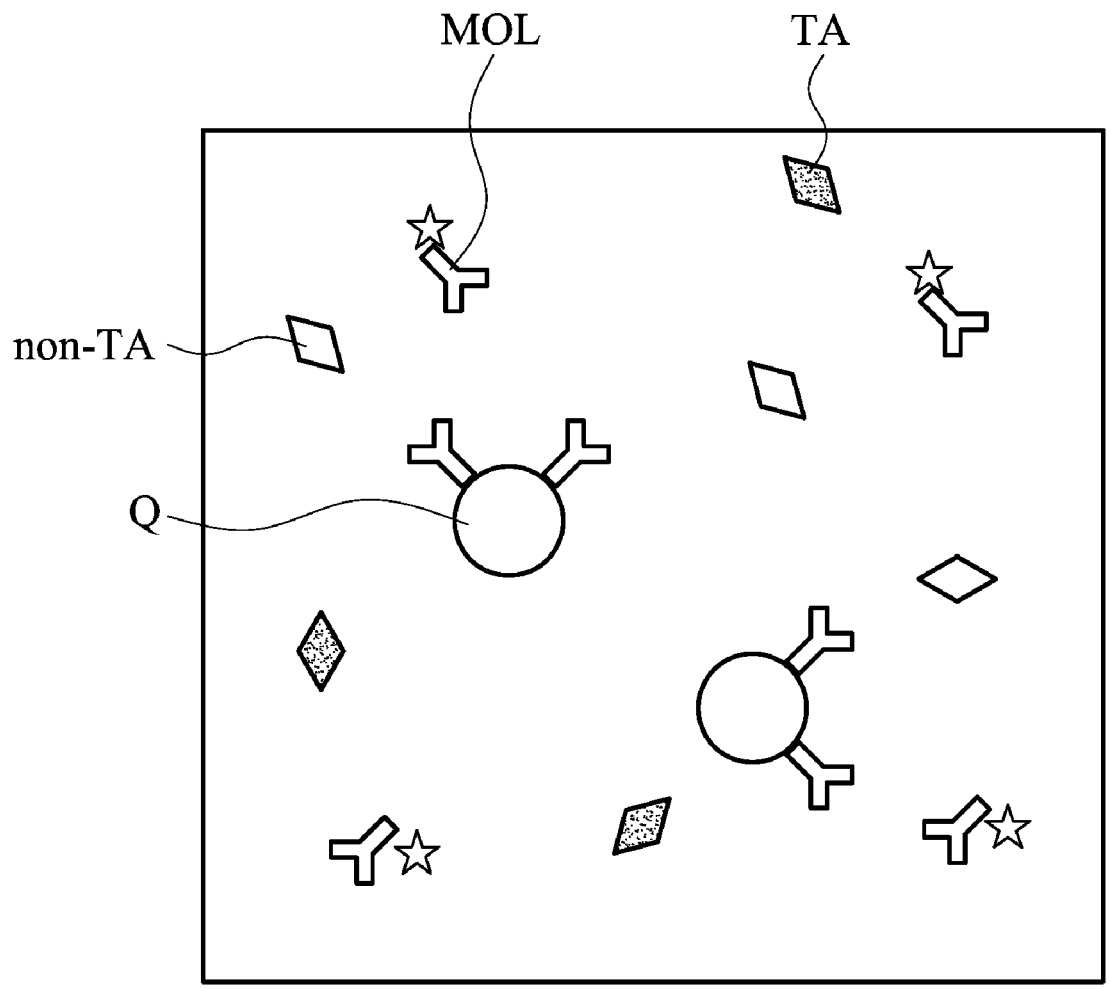
FIGS. 6A to 6C are schematic views of biochemical reaction and optical detection performed by an analytical system of the invention.
Figure 6B:
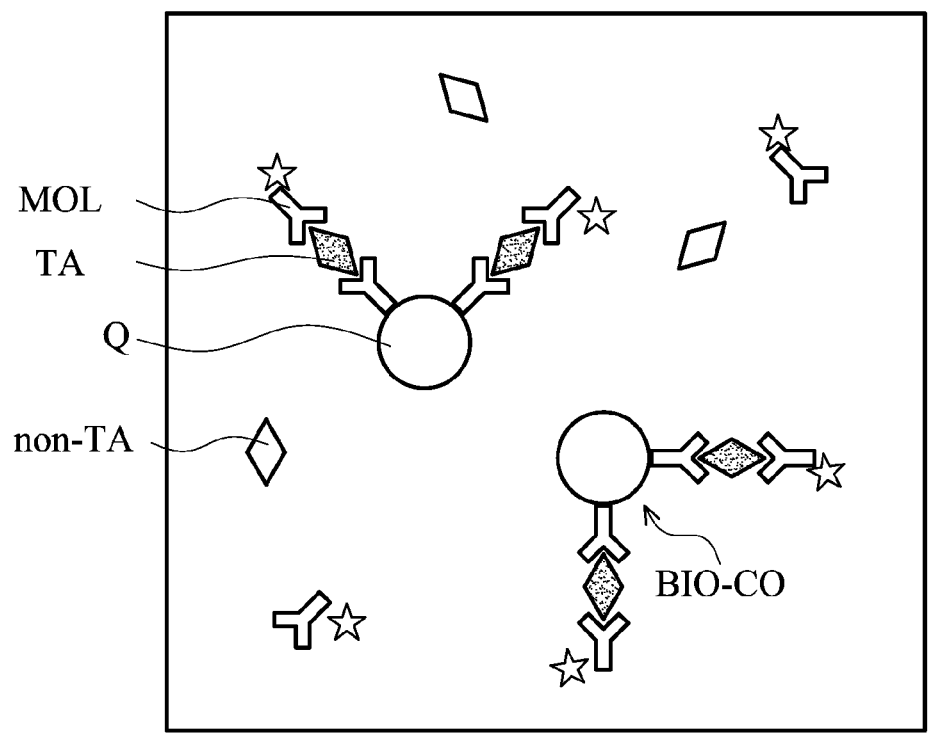
Figure 6C:
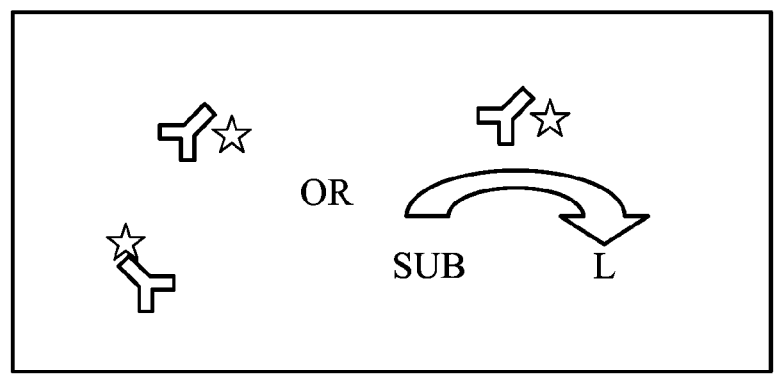

FIGS. 6A, 6B and 6C are schematic views of biochemical reaction and optical detection performed by the analytical system Z of the embodiment.

In FIG. 6A, the objects Q (glass micro-balls) and the target molecules MOL are added in the second compartment C2 (uniformly dividing chamber), and the fluorescent signal within the fifth compartment C5 (detection chamber) can be read from the upper or lower side of the second compartment C2 (uniformly dividing chamber). When a particular target molecule of the tested specimen K appears (see FIG. 6B), the surface-treated object Q (glass micro-ball) can be bonded to the particular target, and then the second reactant carried with the target molecules MOL can be bonded to the connected object Q and the particular target, thus, a bio composite can be formed on the object Q (glass micro-ball). In FIG. 6C, the other unbonded biomoleculars and the target molecules MOL driven by the centrifugal force enter a detection zone. The quantity and concentration of the target molecules MOL can be determined by an optical system located in the fifth compartment C5 (detection chamber) according to the luminous intensity, and the quantity of the target molecules actually reacting with the object Q (glass micro-ball) can be inferred according to the luminous intensity with the known total quantity.

While the invention has been described by way of example and in terms of the several embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A flow structure for performing separation of a tested specimen comprising a first component and a second component with different characteristics therebetween, comprising:
   a main body rotatable about a reference axis penetrating a center thereof;
   a first compartment formed at the center of the main body;
   a second compartment formed in the main body radially outward of the first compartment relative to the reference axis and communicated with the first compartment, wherein the first compartment and second compartments are arranged such that when the tested specimen disposed in the first compartment, an amount of the tested specimen is transmitted from the first compartment to the second compartment;
   a third compartment formed in the main body radially outward of the second compartment relative to the reference axis and communicated with the second compartment, comprising a first cushion region and a second cushion region communicated with the first cushion region, wherein the second compartment and the third compartment are arranged such that rotation of the main body in a first direction for a first predetermined period of time causes the tested specimen located in the second compartment to be transmitted to the first and second cushion regions of the third compartment, and wherein the third compartment is configured such that rotation of the main body in the first direction for a second predetermined period of time subsequent to the first period of time causes the separation of the first and second components of the tested specimen located at the first cushion region such that the second cushion region is filled with the separated first component;
   a fourth compartment formed in the main body and communicated with the third compartment, wherein the third compartment and the fourth compartment are arranged such that the first component of the tested specimen located at the second cushion region is transmitted to the fourth compartment when rotation of the main body is stopped for a particular period of time, and wherein the fourth compartment is configured such that rotation of the main body in a second direction different than the first direction causes the separated first component located at the fourth compartment to be transmitted outwardly relative to the reference axis by an acting force, so that the first component is completely separated from the second component;
   a fifth compartment communicated with the fourth compartment, wherein the separated first component located at the fourth compartment is outwardly transmitted to the fifth compartment by the acting force; and
   a sixth compartment communicated with the fifth compartment.

2. The flow structure as claimed in claim 1 further comprising a first channel communicating the first compartment and the second compartment.

3. The flow structure as claimed in claim 1 further comprising a second channel communicating the second compartment and the third compartment.

4. The flow structure as claimed in claim 3, wherein the second channel is radially distributed with respect to the reference axis.

5. The flow structure as claimed in claim 3, wherein the second channel comprises a capillary channel.

6. The flow structure as claimed in claim 1, wherein the third compartment and the fourth compartment are arranged such that the first component of the tested specimen located at the second cushion region of the third compartment is automatically transmitted to the fourth compartment under a capillary function when the rotation of the main body is stopped.

7. The flow structure as claimed in claim 1, wherein the second cushion region of the third compartment comprises a linear capillary channel.

8. The flow structure as claimed in claim 1, wherein the fourth compartment comprises a linear capillary channel.

9. The flow structure as claimed in claim 1, wherein the second cushion region follows the first cushion region in a flow path, and the first cushion region and the second cushion region of the third compartment define an angle such that the second cushion region turns radially inward relative to the reference axis.

10. The flow structure as claimed in claim 9, wherein the angle is not greater than 30 degrees.

11. The flow structure as claimed in claim 1, wherein the second cushion region of the third compartment and the fourth compartment define an angle turning radially outward relative to the reference axis.

12. The flow structure as claimed in claim 11, wherein the angle is not less than 90 degrees.

13. The flow structure as claimed in claim 1 further comprising a V-shaped transitive channel disposed between the second cushion region of the third compartment and the fourth compartment.

14. The flow structure as claimed in claim 1, wherein the second compartment and the first cushion region of the third compartment are radially distributed with respect to the reference axis.

15. The flow structure as claimed in claim 1, wherein the sixth compartment is communicated with the first cushion region of the third compartment to form a looped flow path between the third, fourth, fifth and sixth compartments.

16. The flow structure as claimed in claim 1, wherein the main body comprises a base surface, and the first compartment, the second compartment, the first cushion region and the second cushion region of the third compartment and the fourth compartment are formed on the base surface of the main body.

17. The flow structure as claimed in claim 16, wherein the depths of the slotted structures of the second cushion region of the third compartment and the fourth compartment are less than that of the first compartment and the first cushion region of the third compartment.

18. The flow structure as claimed in claim 1, wherein the first cushion region of the third compartment comprises a first region communicated with the second compartment and a second region communicated with the first region, and the first compartment and the second compartment define a channel-depth difference.

19. The flow structure as claimed in claim 18, wherein the first cushion region of the third compartment further comprises a middle region located and connected between the first region and the second region, and the first region and the middle region as well as the second region and the middle region define channel-depth differences, respectively.

20. The flow structure as claimed in claim 1, wherein the acting force comprises a Coriolis force generated by Coriolis acceleration.

21. The flow structure as claimed in claim 1, wherein the main body is arranged such that rotation thereof for the first predetermined period of time causes the tested specimen to move by an accelerating motion with respect to the reference axis.

22. The flow structure as claimed in claim 1, wherein the main body is arranged such that rotation thereof for the second predetermined period of time causes the tested specimen is moved by a uniform velocity motion with respect to the reference axis.

23. The flow structure as claimed in claim 1, wherein a specific gravity of the first component is different from that of the second component.

24. The flow structure as claimed in claim 1, wherein the main body comprises a base surface, the first compartment, the second compartment, the first cushion region and the second cushion region of the third compartment, the fourth compartment and the fifth compartment are formed on the base surface of the main body, and the fifth compartment is radially further from the reference axis than the first compartment, the second compartment, the third compartment and the fourth compartment.

25. A flow structure, comprising:
a main body rotatable about a reference axis penetrating a center thereof;
a first compartment formed at the center of the main body;
a plurality of second compartments formed in the main body radially outward of the first compartment relative to the reference axis, each respectively in communication with the first compartment;
a plurality of third compartments, each of the plurality of third compartments formed in the main body and comprising a first cushion region in communication with a respective second compartment and a second cushion region communicated with the first cushion region, wherein the first cushion region is extended radially outwards relative to the reference axis, the second cushion region of the third compartment is substantially extended radially inwards relative to the reference axis, such that the first cushion region and the second cushion region of the third compartment form a first V-shaped path;
a plurality of fourth compartments, each of the plurality of fourth compartments formed in the main body in communication with a respective second cushion region via a respective V-shaped transitive channel and substantially extended radially outwards relative to the reference axis, wherein the second cushion region of the respective third compartment, the respective transitive channel and the respective fourth compartment form a second V-shaped path, such that each respective of the first cushion region and the second cushion region of the third compartment, the transitive channel and the fourth compartment define a flow path from the first cushion region to the fourth compartment that first extends radially outward relative to the reference axis via the first cushion region, then turns radially inwards relative to the reference axis via the second cushion region, and then turns radially outwards relative to the reference axis via the fourth compartment, wherein the flow path does not return to the first compartment; and
a plurality of fifth compartments, each of the plurality of fifth compartments formed in the main body in communication with a respective fourth compartment; and
a plurality of sixth compartments, each of the plurality of sixth compartments formed in the main body in communication with a respective fifth compartment.

26. The flow structure as claimed in claim 25, wherein the main body comprises a base surface, the first compartment, the plurality of second compartments, the plurality of third compartments, the plurality of fourth compartments and the plurality of fifth compartments are formed on the base surface of the main body, and the plurality of fifth compartments are radially further from the reference axis than the first compartment, the plurality of second compartments, the plurality of third compartments and the plurality of fourth compartments.

27. The flow structure as claimed in claim 25, wherein the first compartment and the plurality of second compartments are arranged such that a tested specimen comprising a first component and a second component with different characteristics therebetween is transmitted from the first compartment to each of the plurality of second compartments when the tested specimen is disposed in the first compartment, the plurality of second compartments and the plurality of third compartments are arranged such that rotation of the main body in a first direction for a first predetermined period of time causes the tested specimen located at each one of the plurality of second compartments to be transmitted to a respective one of the plurality of third compartments, rotation of the main body in the first direction for a second predetermined period of time causes separation of the first and second components of the tested specimen located at the first cushion region of each of the plurality of third compartments such that second cushion region of each of the plurality of third compartments is filled with the separated first component, wherein the first predetermined period of time is prior to the second predetermined period of time;
wherein third compartment and the fourth compartment are arranged such that the first component of the tested specimen located at the second cushion region of each of the plurality of third compartments is transmitted to a respective one of the plurality of fourth compartments via the respective transitive channel when rotation of the main body is stopped for a particular period of time; and
wherein the plurality of fourth compartments are configured such that the separated first component located at each of the plurality of fourth compartments is outwardly transmitted by an acting force to a respective one of the plurality of fifth compartments when the main body rotates in a second direction opposite to the first direction, such that the first component is completely separated from the second component.

28. The flow structure as claimed in claim 25, wherein the main body comprises a base surface, and the first compartment, the plurality of second compartments, the plurality of third compartments and the plurality of fourth compartments are formed on the base surface of the main body.

29. The flow structure as claimed in claim 25, wherein the first compartment is communicated to each of the plurality of second compartments by a respective first channel, and each of the second compartments is communicated to a respective third compartment by a respective second channel.

30. A flow structure, comprising:
a main body rotatable about a reference axis penetrating a center thereof;
a first compartment formed at the center of the main body;
a plurality of first path portions formed in the main body radially outward of the first compartment relative to the reference axis, each of the plurality of first path portions comprising a second compartment communicated with the first compartment; and
a plurality of second path portions formed as looped paths communicated with a corresponding one of the plurality of second compartments, each of the plurality of second path portions comprising:
a third compartment comprising a first cushion region communicated with the corresponding second compartment and a second cushion region communicated with the first cushion region, wherein the first cushion region is extended outwards relative to the reference axis, and the second cushion region is substantially extended inwards relative to the reference axis; and
a fourth compartment communicated with the second cushion region of the third compartment via a transitive channel and substantially extended outwards relative to the reference axis;
a fifth compartment communicated with the fourth compartment; and
a sixth compartment communicated with the fifth compartment and the first cushion region of the third compartment.

31. The flow structure as claimed in claim 30, wherein the main body comprises a base surface, wherein the first path portions and second path portions are formed on the base surface of the main body, and wherein each fifth compartment is radially further from the reference axis than the first compartment, each second compartment, each third compartment and each fourth compartment.

32. The flow structure as claimed in claim 30, wherein the flow structure is utilized to perform separation of a tested specimen comprising a first component and a second component with different characteristics therebetween, the tested specimen is transmitted from the first compartment to each second compartment when the tested specimen is disposed in the first compartment, rotation of the main body in a first direction causes the tested specimen located at each second compartment to be transmitted to the plurality of third compartment communicated thereto at a first predetermined period of time, separation of the first and second components of the tested specimen located at the first cushion regions of each third compartment is performed at a second predetermined period of time, wherein the first predetermined period of time is prior to the second predetermined period of time, and the second cushion regions of each third compartment is filled with the separated first component;
wherein the first component of the tested specimen located at the second cushion regions of each third compartment is transmitted to the fourth compartment communicated thereto via the transitive channels when rotation of the main body is stopped with respect to the reference axis and delayed after a particular period of time, wherein the separated first component located at each fourth compartment is outwardly transmitted by an acting force via each fourth compartment when rotation of the main body that was stopped begins to rotate in a second direction opposite to the first direction, such that the first component is completely separated from the second component; and
wherein the separated first component located at each fourth compartment is outwardly transmitted to the fifth compartment communicated thereto by the acting force when rotation of the main body that was stopped begins to rotate in the second direction, such that the first component is completely separated from the second component.

33. The flow structure as claimed in claim 30, wherein each of the plurality of first path portions further comprises a first channel communicated between the first compartment and the second compartment and a second channel communicated between the second compartment and the corresponding third compartment.

* * * * *